US005789173A

United States Patent [19]
Peck et al.

[11] Patent Number: 5,789,173
[45] Date of Patent: Aug. 4, 1998

[54] METHODS FOR RAPID ANTIMICROBIAL SUSCEPTIBILITY TESTING

[75] Inventors: Konan Peck; Pan-Chyr Yang, both of Taipei; Shu-Li Wung, Taipei Hsien, all of Taiwan

[73] Assignee: Academia Sinica, Taipei, Taiwan

[21] Appl. No.: 692,008

[22] Filed: Aug. 2, 1996

[51] Int. Cl.⁶ ........................................ C12Q 1/68
[52] U.S. Cl. .................... 435/6; 435/7.2; 435/7.21; 435/7.31; 435/7.32; 435/7.91; 435/32; 436/518; 436/530; 436/809; 536/25.3; 536/25.31; 536/25.32; 536/25.4; 536/25.41; 356/201; 356/442
[58] Field of Search ..................... 435/7.2, 7.32, 435/7.4, 14, 18, 19, 21, 29, 38, 34, 32, 967, 970, 973, 975, 6, 7.21, 7.31, 7.91; 356/442, 201; 436/518, 530, 809; 536/25.3, 25.31, 25.32, 25.4, 25.41

[56] References Cited

U.S. PATENT DOCUMENTS

| | | | |
|---|---|---|---|
| 4,385,115 | 5/1983 | de Zabala et al. | 435/33 |
| 4,622,297 | 11/1986 | Kappner et al. | 435/32 |
| 4,683,195 | 7/1987 | Mullis et al. | 435/6 |
| 4,778,758 | 10/1988 | Ericsson et al. | 435/32 |
| 4,861,709 | 8/1989 | Ulitzur et al. | 435/6 |
| 5,059,522 | 10/1991 | Wayne | 435/7.2 |
| 5,089,395 | 2/1992 | Snyder et al. | 435/39 |
| 5,091,652 | 2/1992 | Mathies et al. | 250/458.1 |
| 5,112,745 | 5/1992 | Lorr | 435/38 |
| 5,288,611 | 2/1994 | Kohne | 435/6 |
| 5,316,918 | 5/1994 | Ollar | 435/34 |
| 5,348,854 | 9/1994 | Webster, Jr. et al. | 435/6 |
| 5,422,242 | 6/1995 | Young | 435/6 |
| 5,567,587 | 10/1996 | Kohne | 435/6 |
| 5,601,984 | 2/1997 | Kohne | 435/6 |
| 5,612,183 | 3/1997 | Kohne | 435/6 |

FOREIGN PATENT DOCUMENTS

| | | |
|---|---|---|
| 0187 332 A2 | 7/1986 | European Pat. Off. |
| 0 457 685 A1 | 11/1991 | European Pat. Off. |
| 0 534 640 A1 | 3/1993 | European Pat. Off. |
| WO 84/02721 | 7/1984 | WIPO |
| WO 89/07606 | 8/1989 | WIPO |
| WO 95/34574 | 12/1995 | WIPO |

OTHER PUBLICATIONS

Guatelli et al., 1990, "Isothermal in vitro amplification of nucleic acids by a multienzyme reaction modeled after retroviral replication" P.N.A.S. (USA) 87:1874–1878.

Walker et al., 1992, "Strand displacement amplification—an isothermal, in vitro DNA amplification technique" Nucleic Acids Res. 20(7):1691–1696.

Wilson et al., 1990, "Amplification of Bacterial 16S Ribosomal DNA with Polymerase Chain Reaction" J. Clin. Microbiology 28(9):1942–1946.

Boddinghaus et al., 1990, "Detection and Identification of Mycobacteria by Amplification of rRNA" J. Clin. Microbiology 28(8):1751–1759.

Glazer et al., 1992, "Stable dye–DNA intercalation complexes as reagents for high–sensitivity fluorescence detection" Nature 359:859–861.

Greisen et al., 1994, "PCR Primers and Probes for the 16S rRNA Gene of Most Species of Pathogenic Bacteria, Including Bacteria Found in Cerebrospinal Fluid" J. Clin. Microbiology 32(2):335–351.

Waitz et al., 1990, "Methods for dilution antimocribial susceptibility tests for bacteria that grow aerobically—2nd edition" NCCLS Document M7–A2 vol. 10(2).

Kahn et al., "A reverse transcriptase–PCR based assay for in–vitro antibiotic susceptibility testing of Chlamydia pneumoniae" J. Antimicrobial Chemotherapy (1996) 37:677–685.

Glazer et al., "Stable dye–DNA intercalation complexes as reagents for high–sensitivity fluorescence detection" Nature (1992) 259:859–861.

*Primary Examiner*—James O. Wilson
*Attorney, Agent, or Firm*—McDonnell Boehnen Hulbert & Berghoff

[57] ABSTRACT

The present invention discloses a method for rapid antimicrobial susceptibility testing to screen antibiotics in a few hours instead of days by conventional methods. This method can also be used to identify susceptible antibiotics to treat mycobacterial infection in a few days instead of the usual six to eight weeks. Fast screening of antibiotics is achieved by a short period of specimen incubation in different antibiotics embedded media to create differential bacterial counts. The differences of bacterial counts among antibiotics embedded media are subsequently amplified by DNA amplification methods for detection. Following DNA amplification, rapid quantitation and minimum inhibition concentration (MIC) determinations for a panel of antibiotics are achieved in less than one minute by fluorescence quantitation methods.

34 Claims, 3 Drawing Sheets

METHODS FOR RAPID ANTIMICROBIAL SUSCEPTIBILITY TESTING

BACKGROUND OF THE INVENTION

1. Field of Invention

This invention relates to methods for rapidly identifying and quantitating efficacious antimicrobial agents.

2. Description of Prior Art

In recent years, the emergence of strains of drug-resistant bacteria has become a major health problem in many parts of the world. This has made it vitally necessary both to develop new antibacterial drugs and establish effective strategies to combact invading bacteria.

Presently, to treat patients afflicted with severe microbial infections, a random guessed broad spectrum antibiotics often fails to yield satisfactory results.

Antimicrobial susceptibility testing often be used to determine the right antimicrobial agents. It takes two to three days to complete the test, either by dilution method or by diffusion method. For frail or immuno-suppressed patients already in the process of developing septic shock, finding the right antibiotics in time is critical, because many of the patients could not survive the three-day period required by conventional antimicrobial susceptibility testing.

Traditional susceptibility testing methods rely on observation of bacterial colony formation, which requires prolonged incubation in order to accumulate sufficient mass to be visible. (See for example, "Methods for Dilution Antimicrobial Susceptibility Tests for Bacteria that Grow Aerobically" NCCLS Document M7-A2, 10(8), 2nd eds., 1990.)

There are many methods and instruments developed to identify bacterial pathogens with shorter time intervals; see for example, U.S. Pat. No. 4,385,115 issued to Hoffmann-La Roche Inc. N.J., U.S.A; U.S. Pat. No. 5,112,745 issued to Space Medical System, Inc., Garrett Park, Md.; U.S. Pat. No. 5,089,395 issued to Univ. of Cincinnati, Cincinnati, Ohio; and U.S. Pat. No. 5,059,522 issued to L. G. Wayne, Irvine, Calif.

Nevertheless, pathogen identification does not necessarily provide information of what antibiotic drug yields pathogen susceptibility. For most of the nosocomial or community acquired bacterial infections, the pathogens are indigenous flora rather than epidemic pathogens that cause, for example, cholera or typhus and must be reported to government health administrations. For most physicians and patients, identification of the antimicrobial agent which can cure the illness is more important in therapeutics than knowing the nature of the pathogen itself.

In conventional antimicrobial susceptibility testing whether it is the micro-dilution or the disk diffusion method, primary culture of specimens on agar plates is required in order to observe the bacterial growth and identify the pathogen species. Subcultures are then performed to enrich bacterial population. For many types of conventional susceptibility testing, a standard concentration of bacterial inoculum must be used. The concentration of bacteria in a liquid medium can be determined in several ways including measurement of the optical density of a broth culture or by comparing the turbidity of a liquid medium to a standard representing a known number of bacteria in suspension. To test for susceptibility of pathogens to antimicrobial agents, the standardized inoculum is mixed with various antibiotics of different concentrations and the susceptibility is determined by visual examination of bacterial growth.

Newer methods using instruments to detect bacterial growth based on photometric detection of broth turbidity, radiometric detection of bacterial metabolites, or fluorometric detection of hydrolyzed fluorogenic substrates incorporated in culture medium (see e.g. C. Thornsberry et al., J. Clin Microbiol. 12, 375 (1980); F. S. Nolte et al., J. Clin. Microbiol. 26, 1079 (1988); J. L. Staneck et al., J. Clin. Microbiol. 22, 187 (1985); P. G. Beckwith et al., J. Clin. Microbiol. 15, 35 (1982)) have reduced the incubation time to a few hours.

Despite the improvements in instrumentation, all the prior art require primary culture and subculture routines which enrich bacterial concentrations to levels sufficiently high to be standardized by visual methods such as McFarland nephelometry. This inevitable procedure of inoculum concentration standardization is due to the fact that minimum inhibition concentration (MIC) of antibiotics is dependent on inoculum concentration in the prior art.

Superisingly, the invention has found that antimicrobial susceptibility testing can be conducted without the need of primary culture of specimen, or knowing the identity of the pathogen. Identification of the pathogen, however, can be done in parallel by conventional methods, if necessary.

SUMMERY OF THE INVENTION

It is an object of this invention to provide a rapid antimicrobial susceptibility testing method without primary culture process.

It is another object of this invention to perform antimicrobial susceptibility testing without prior species identification of microbes.

It is another object of this invention to determine MIC values without standardization of inoculum concentration.

It is another object of this invention to provide fast antimicrobial susceptibility testing for well known slow growing microorganisms such as fungi and mycobacteria.

It is a further object of this invention to rapidly determine MIC values by simultaneously detecting a large number of PCR products in minutes.

BRIEF DESCRIPTION OF THE DRAWINGS

The accompanying drawings, which are incorporated in and form a part of this specification, illustrate embodiments of the invention and, together with the description, serve to explain the principles of the invention.

DETAILED DESCRIPTION OF THE INVENTION

The invention in the first aspect provides a method for rapid antimicrobial susceptibility testing, which comprises the steps of:

(a) incubating specimens of human body fluids, blood, and others containing microbe(s) in media embedded with antimicrobial agents of serial dilution concentrations for a short time to create differential microbial counts;

(b) amplifying the differential microbial counts by in vitro microbial DNA replication;

(c) adding reporter molecules which are specific to double stranded DNA (dsDNA) and form complexes therewith; and (d) observing the presence or absence of signal emission from the reporter molecule-dsDNA complexes.

Figure 1:
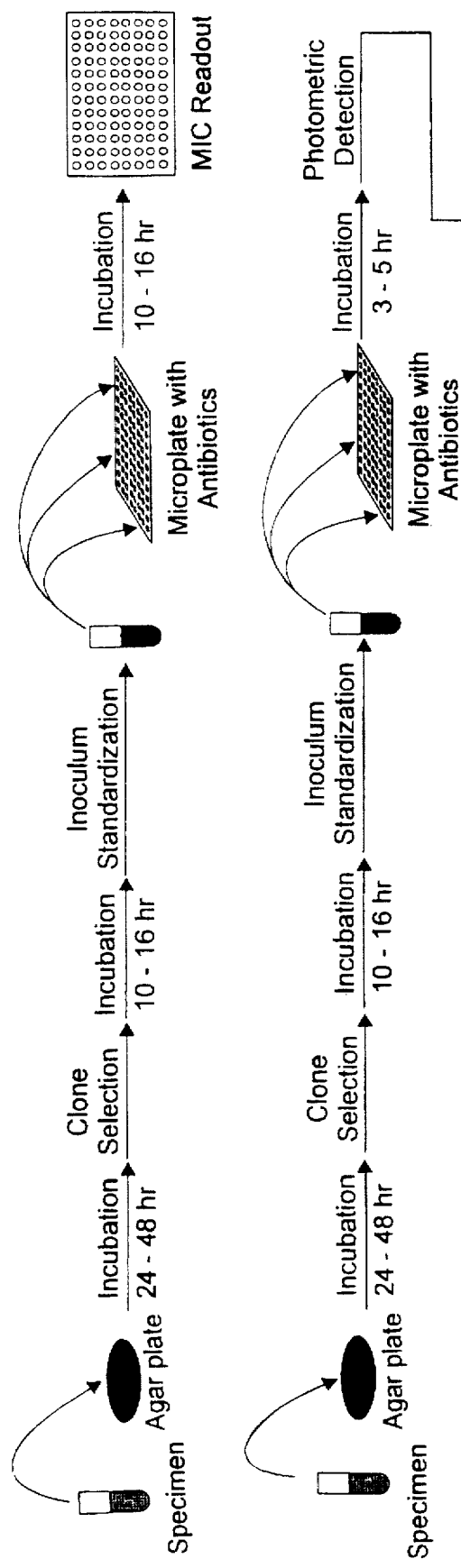
FIG. 1 shows the comparison between two conventional antimicrobial susceptibility testing methods and the invention in terms of steps and time consumed.
Figure 1:
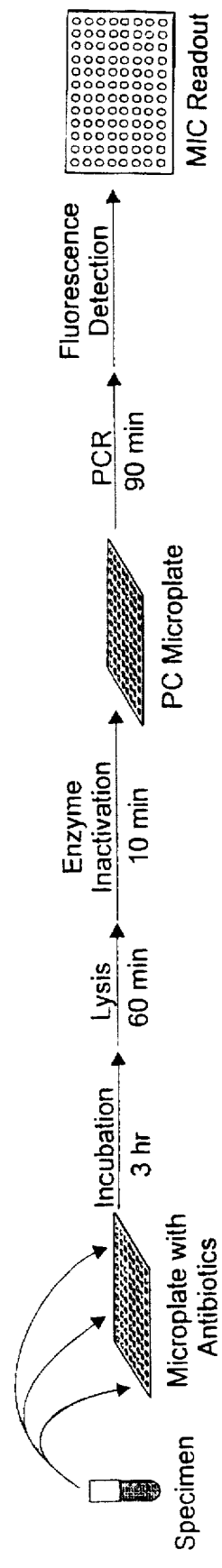

FIG. 1 depicts the differences between two conventional antimicrobial susceptibility testing methods and the invention in terms of steps and time consumed. As clearly shown, the method in accordance with the invention avoids the primary culture process to incubate specimen directly in antibiotics embedded media without standardizing bacterial concentration. Also, the method in accordance with the invention rapidly identifies efficacious antimicrobial agents against pathogens without prior knowing the identity of the pathogens.

In a further aspect, the invention provides a method for determining the MIC values of antimicrobial agents which comprises the steps of:

(a) incubating specimens of human body fluids, blood, and others containing microbe(s) in media embedded with antimicrobial agents of serial dilution concentrations for a short time to create differential microbial counts;

(b) amplifying the differential microbial counts by in vitro microbial DNA replication;

(c) adding reporter molecules which are specific to dsDNA and form complexes therewith; and (d) recording the lowest concentration of antimicrobial agents which does not result in signal emission from the reporter molecule-dsDNA complexes as the MIC values.

Figure 2:
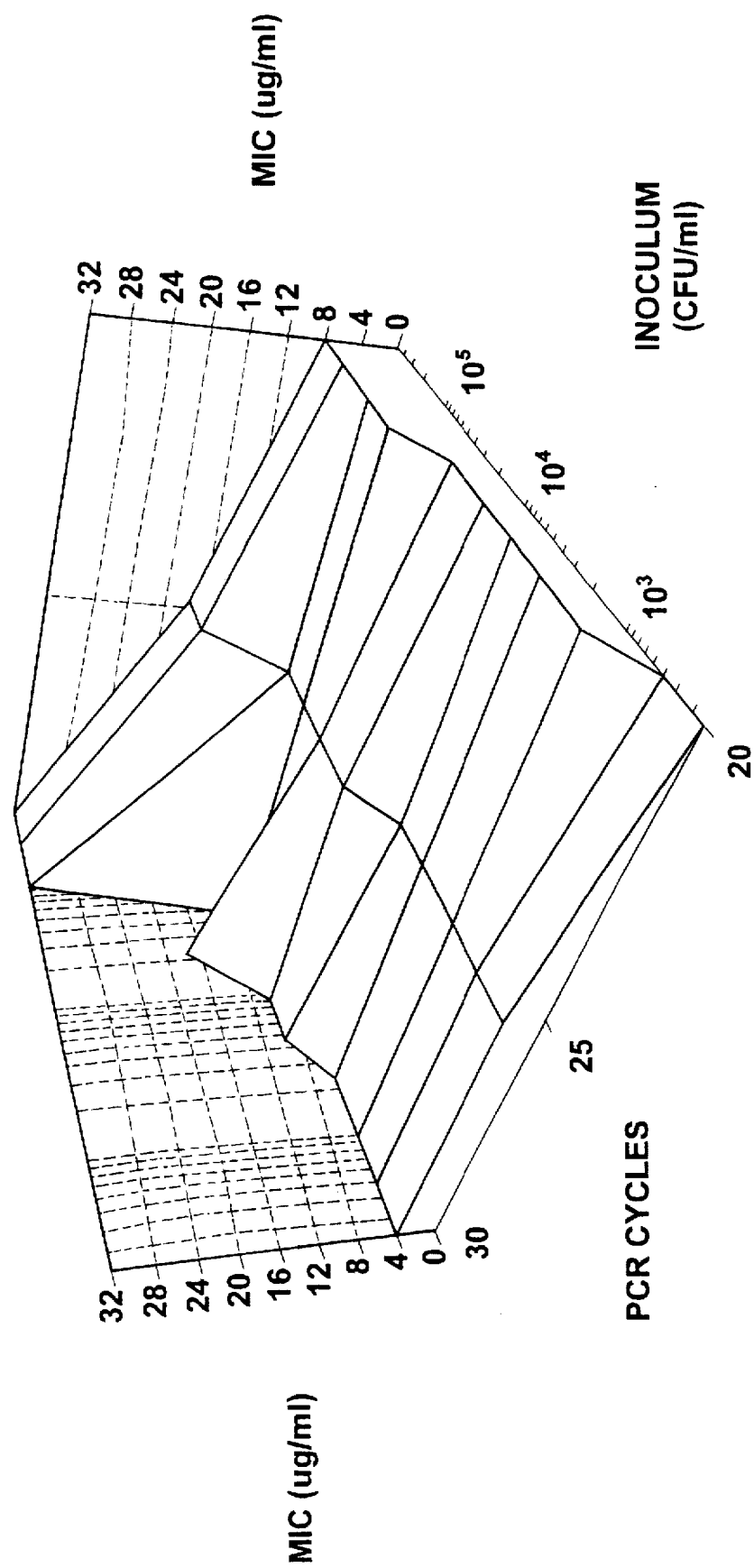
FIG. 2 shows MIC value vs. PCR cycle number and inoculum concentration to demonstrate that the MIC value is independent of inoculum concentration at low concentrations.

In accordance with the method of this invention, MIC values are dependent on bacterial concentration only at high bacterial concentrations. The system of the invention thus evades the lengthy primary culture procedures in an innovative way. This concept is further taught and validated by FIG. 2 to show that the MIC values are independent of PCR amplification cycles and concentration of bacteria at low inoculation concentrations. At concentrations as high as $1 \times 10^6$ CFU/ml which are about 1/100 of the inoculation concentration, 0.5 McFarland standard ($1.5 \times 10^8$ CFU/ml), used in prior art, the MIC values vary with inoculum concentration as shown in FIG. 2.

To incubate specimens in antibiotics embedded media, any incubation containers conventionally used are suitable. In this regard, 96-well microtiter plates can be conveniently used. Each column of a 96-well plate contains culture medium (such as Mueller-Hinton broth) together with one antibiotic at various concentrations in eight different rows. Therefore, with one column reserved for controls, one 96-well microtiter plate can be used to test eleven different essential antibiotics at 8 different concentrations.

Contrary to the lengthy incubation period of the prior art, the incubation time of this invention can be significantly reduced. The suitable incubation time for bacteria in accordance with the invention can range from 1-12 hours. Preferably, it is within 1-6 hours. The most preferred incubation time is as short as three hours.

Taking *Escherichia coli* for example, its replication time is twenty minutes during logarithmic growth phase. In three hours, the bacterial count increases 512 times in the wells containing inefficacious antimicrobial agents. On the other hand, wells containing efficacious antimicrobial agents or effective concentrations would yield no bacterial growth.

For some fastidious bacteria such as Haemophilus species or *N. gonorrhoeae*, the Mueller-Hinton broth may require supplementation to support the growth of the bacteria. To compensate for these possible false negative results due to fastidious bacteria, a column of micro-wells may be reserved to contain DNA amplification primers specific to the fastidious bacteria species and medium supplements.

The method of the invention is also applicable to susceptibility testing for slow growing microorganisms such as fungi or mycobacteria.

Accordingly, the invention in another aspect provides a method for fast antimicrobial susceptibility testing for slow growing microorganisms, which comprises the steps of:

(a) incubating specimens containing slow growing microorganisms in media embedded with antimicrobial agents of serial dilution concentrations for a sufficient time to create differential microbial counts;

(b) amplifying the differential microbial counts by in vitro microbial DNA replication;

(c) adding reporter molecules which are specific to double stranded DNA (dsDNA) and form complexes therewith; and (d) observing the presence or absence of signal emission from the reporter molecule-dsDNA complexes.

In this application, antifungal agents such as Fluconazole, Nystatin, Amphotericin B, etc., are used instead of antibacterial agents for fungal antimicrobial susceptibility testing, and longer incubation time will be required due to the nature of the microorganisms. For antimicrobial susceptibility testing of the well known slow growing *Mycobacterium tuberculosis*, the incubation time is increased to 6 days and anti-tuberculosis drugs such as rifampin, isoniazid, and ethambutol are used instead.

The susceptibility testing results can be obtained in one to several days. Preferably, the results are obtained in one day for fungi, and less than 10 days for mycobacteria, as compared with the usual 6 to 8 weeks required by prior art.

Since this invention teaches revolutionary concepts to evade time consuming primary culture and species identification, in order to distinguish bacterial infection from fungal or mycobacterial infection when the results show resistance to all the antibacterial agents being tested, two micro-wells containing no antibiotics but DNA amplification primers specific to fungi and mycobacteria, respectively, are needed.

Specimens from different human systems also require different treatments. For example, specimens collected from sites of abscess or urinary tracts require dilution while blood or cerebrospinal fluid (CSF) specimens need additional two to three hour enrichment incubation to overcome the statistical thresholds.

In order to rapidly remove pathogens from the blood and its antibacterial properties together with antimicrobial agents that were applied to patients, lysis centrifugation by using an Isolator system (Wampole Lab, Cranbury, N.J.) can be a suitable method. The blood cells are lysed in a glass tube and the content is centrifuged at $3,000 \times g$ for 30 minutes to precipitate the pathogens.

Because the number of bacterial counts is typically very small in blood specimens, in order to avoid zero pathogens in any micro-well, the blood specimens need additional enrichment culture. To save time, breakpoint susceptibility testing rather than MIC test to determine whether the pathogen is susceptible, intermediate, or resistant to various antimicrobial agents may be more practical for patients in critical condition. In this manner, 20 micro-wells are sufficient to test 10 different antibiotics.

According to Poisson distribution calculation, in order to have less than 10% probability of having zero bacteria in any well, each well must have, on average, 3 bacterial counts. For most of the common bacterial pathogens, especially for those exist in normal flora, a three-hour enrichment incubation should be sufficient to gain enough bacterial counts to overcome the statistical barrier.

To test for antimicrobial susceptibility or to measure the MIC values, a short period of incubation in antimicrobial agent embedded medium creates necessary differential bacterial counts but the number is too low to be detected, either visually or with instruments.

To amplify the difference, the prior art use the time consuming cell culture to replicate bacteria. This invention, however, amplifies the difference by in vitro DNA replication, e.g. in vitro amplification of the common 16S rRNA gene among bacteria.

DNA amplification methods such as polymerase chain reaction (PCR), strand displacement amplification, and self-sustained sequence replication have been used to replicate 16S rRNA gene specific to different bacteria for genera or species identification. (See for examples, "Amplification of Bacterial 16S Ribosomal DNA with Polymerase Chain Reaction" Wilson et al., J. of Clin. Microbiol., 28(9), 1942–1946, 1990; "Strand Displacement Amplification—an Isothermal, in vitro DNA amplification techniques" Walker et al., Nucleic Acids Res., 20(7), 1601–1696, 1992; and "Isothermal, in vitro amplification of nucleic acids by a multienzyme reaction modeled after retroviral replication" Guatelli et al., Proc. Natl. Acad. Sci. USA, 87, 1874–1878, 1990.) In addition, PCR primers and probes for the 16S rRNA gene of most species of pathogenic bacteria have been reported in Greisen et al., J. of Clin. Microbiol., 32(2), 335–350, 1994. All publications with the entire contents are incorporated into the references of the invention.

This invention, however, teaches new applications of these in vitro amplification methods to replicate conserved region of 16S rRNA gene for antimicrobial susceptibility testing.

To expose the bacterial genetic material for amplification, the microorganisms are lysed with lysing reagents. Suitable lysing agents for exposing genomic DNA or RNA for amplification include, but not limited to, lysozyme and proteinase K.

To amplify bacterial DNA, the prior art require that the bacteria be purified from culture medium before the lytic reagents are applied. After bacterial cells are lysed, the lytic reagents must be removed before the DNA amplification can proceed because the amplification process requires DNA polymerases that are vulnerable to lytic reagents. However, to purify a large number of samples in microtiter plate format is not practical and is time consuming. This invention teaches that diluting the culture medium or the lytic reagents by 10-fold is sufficient to reduce the various inhibiting components to levels that do not interfere with the amplification process.

Therefore, after exposing genetic material of microorganisms, amplification can be performed directly without removing ingredients, e.g. lytic agents, in the culture medium by centrifugation or other purification processes.

The in vitro DNA amplification methods achieve one round of DNA replication in less than three minutes. In comparison, for fast growing bacterium like *E. coli*, the traditional cell culture method requires 20 minutes for one round of replication and approximately 20 hours for slow growing bacterium like *M. tuberculosis*.

DNA amplification can be conducted either by polymerase chain reaction for preferably less than 30, e.g. 25 cycles, in a multi-well PCR machine, or by other DNA replication methods, e.g. isothermal in vitro amplification, for less than four hours, preferably less than three and most preferably less than two hours.

To analyze DNA molecules amplified by PCR or other DNA amplification methods, electrophoresis is the conventional method of choice. By identifying a band on a slab gel one can determine whether the DNA amplification reaction has generated the desired product. This analytical method is acceptable when only a few samples are analyzed. In antimicrobial susceptibility testing or in other screening methods where large number of samples are employed on a microtiter plate, using electrophoresis as the analytical tool is intolerably tedious and impractical. This invention recognizes the limitations which arise from a large number of DNA amplification product analysis and provides a quick solution to solve the problem.

There are many ways to distinguish dsDNA molecules from free deoxynucleotides by their physical properties such as absorbance (hypochromacity) or circular dichroism. (See e.g. D. Freifelder, Physical Biochemistry, 2nd Ed. W. H. Freeman & Co.) However, drawing samples one by one and measuring them spectrophotometrically does not improve in detection speed over that of gel electrophoresis. Newer PCR product analyzing methods utilizing electro-chemiluminescence principles or enzyme calorimetric detection principles to simultaneously detect large number of PCR products are available. (See e.g. Miller, L. A. et al., J. Clin Microbiol. 32(5), 1373–1375, 1994; and Roy, Y. R. et al., J. Clin. Microbiol. 22(3), 467–469, 1995.) However, these methods require blocking, incubation, and washing procedures which can delay the process of susceptibility testing.

In accordance with the invention, reporter molecules which are specific to dsDNA and form complexes therewith are utilized to distinguish the dsDNA generated by DNA replication methods from the free nucleotides dominating in the wells that contain efficacious antimicrobial agent. The signal emission from the complexes provides an efficient means for an immediate visual determination of which wells have gone through DNA amplification to contain high bacterial DNA concentrations.

Some fluorescent intercalating dyes selectively bind to dsDNA and give out enhanced fluorescence emission when bound. Stable dye-DNA intercalation complexes as reagents for high-sensitivity fluorescence detection have been reported in Glazer, A. N., Rye, H. S., Nature, 359, 859–861, 1992. The intercalating dyes of choice are, for example, 1,1'-(4,4,7,7,-tetramethyl-4,7-diazaundecamethylene)-bid-4-[3-methyl-2,3-dihydro-(benzo-1,3-thiazo)-2-methylidene]-quinolinium tetraiodide, designated TOTO or 1,1'-(4,4,7,7-tetra-methyl-4,7-diazaundecamethylene)-bis-4-[3-methyl-2,3-dihydro-(benzo-1,3-oxazole)-2-methylidene]-quinolinium tetraiodide, designated YOYO. These dyes allow much more sensitive fluorescence detection of double stranded DNA than previously possible.

The fluorescence emission enhancement of YOYO or TOTO when bound to dsDNA are on the order of thousands, the $F_{bound}$ vs. $F_{free}$ is 3200 for YOYO and 1100 for TOTO. Compared to ethidium bromide ($F_{bound}/F_{free}$ ~30) which is the most widely used intercalating dye for detecting dsDNA, YOYO or TOTO offers much higher signal-to-noise ratio in detection. Therefore, by using intercalating dye with very high fluorescence enhancement ratio, one can distinguish, by fluorescence intensity, wells that contain dsDNA from those that do not.

Intercalating dyes such as propidium iodide or ethidium homodimer can also be used for rapid detection of DNA amplification. Because ethidium bromide has larger absorptivity in the UV range than YOYO, ethidium bromide appears to have brighter fluorescence emission than YOYO when UV transillumination light box is used as the excitation source. However, ethidium bromide has much lower $F_{bound}$ vs. $F_{free}$ ratio than YOYO. Therefore, the background emission of free ethidium bromide is significantly higher than free YOYO so that the dynamic range and signal-to-noise ratio of detection are less with ethidium bromide. This lower UV absorptivity of YOYO can be overcome by using blue light wavelengths ranging between 450–490 nm to excite the dye. The light source can either be a high power xenon lamp or tungsten halogen lamp with a bandpass filter optimized to pass excitation wavelengths from 450 nm to 490 nm or a laser with output ranging within that particular wavelength region, for instance, an argon ion laser with 488 nm output.

To generate and measure fluorescence emission from individual well, a laser induced fluorescence microtiter plate reader can be used. By using laser induced fluorescence detection, the fluorescence emissions from the micro-wells are sufficiently intense such that minimal signal integration time is required and a microtiter plate containing 96 samples can be read in less than 20 seconds.

The detection method in accordance with the invention using intercalating dye is rather simple. After the amplification reaction is done, the dye such as ethidium bromide can be pipetted in the container, e.g. a microtiter plate, and the container is placed over a UV trans-illumination light box. The wells that contain amplified dsDNA will lit up brightly while the other wells remain dim. Using either of these powerful intercalating dyes, 96 amplified samples can be detected on a microtiter plate in just a few seconds by observing the plate with one's eyes.

Alternatively, the microtiter plate can be read by a fluorescence microtiter plate reader with Xenon arc lamp as the excitation source. The intensity of the fluorescence or the concentration of the bacteria in the wells can be quantitated with appropriate fluorescence bandpass filters.

To have quantitative data, fluorescent intercalating dyes such as ethidium bromide, SYBR I, or YOYO is added to each well either before or after the amplification reaction. Fluorescence intensities from the wells that contain efficacious antimicrobial agents are low due to few or no replication templates while the wells that contain inefficacious antimicrobial agents yield high fluorescence intensities.

For quantitative purpose, controls in two microtiter wells are needed. The signal arising from the well containing no antimicrobial agent but culture medium alone represents full scale growth with no inhibition. The signal arising from the well containing lytic agents such as lysozyme represents zero growth. To assure good linear correlation between fluorescence intensity and bacterial counts in wells, quantitative DNA amplification must be performed within a linear range, which means sample dilution and a low number of amplification cycles must be employed.

To report results, the lowest antimicrobial concentration to have the same fluorescence intensity as the zero growth control is recorded as the Minimum Inhibition Concentration (MIC).

The entire process, from the placement of specimens in microtiter wells to the retrieval of MIC values, can be completed in less than 6 hours. Compared to the traditional broth dilution or disk diffusion methods which require visual detection of bacterial colonies, this novel system is 10-fold faster. Furthermore, this system is applicable to antimicrobial susceptibility testing for fungal or mycobacterial infections. The results of susceptibility testing can be obtained in one day for fungi and less than 10 days, compared to the routine 6 to 8 weeks as required by prior art, for mycobacteria.

Taken altogether, this innovative system is an integrated approach to identify efficacious antimicrobial agents which save lives of many critically ill bacteremia patients. Particularly at the time when drugs which effectively control sepsis are yet to be discovered, eradicating pathogens in good time will prevent patients from developing septic shock and increase the odds of survival from the infection.

Without further elaboration, it is believed that one skilled in the art can, using the preceding description, utilize the present invention to its fullest extent. The following examples are, therefore, to be construed as merely illustrative, and not limitative of the remainder of the disclosure in any way.

EXAMPLE 1

To demonstrate and realize the invention, Escherichia coli ATCC 25922 as recommended by NCCLS (National Committee for Clinical Laboratory Standards) was used. The strain is genetically stable and has tabulated MIC ranges published by NCCLS as follows for ampicillin, cephalothin, nalidixic acid and gentamicin.

| Quality control MIC range E. coli ATCC 25922 | |
|---|---|
| Antibiotics | MIC range µg/ml) |
| Ampicillin | 2.0–8.0 |
| Cephalothin | 4.0–16.0 |
| Nalidixic Acid | 1.0–4.0 |
| Gentamicin | 0.25–1.0 |

One hundred µl of E. coli, ATCC 25922, inoculum with concentrations approximately $2.5 \times 10^4$ CFU/ml in Mueller-Hinton broth was inoculated in each well of a 96-well microtiter plate. The stock solutions of the antibiotics were prepared according to NCCLS recommendations. Appropriate concentrations of each kind of the following antimicrobial agent was added to the first row of the microtiter plate. Serial 2-fold dilutions of the antimicrobial agents being tested was performed in each row to generate eight rows of varying antimicrobial concentrations: ampicillin (0.25–32 µg/ml); cephalothin (0.5–32 µg/ml); gentamicin (0.125–16 µg/ml; and nalidixic acid (0.25–32 µg/ml).

Following a 3-hour incubation interval at 37° C., 3 µl amount of each well sample was transferred to a V-bottom autoclavable microtiter plate for further treatment.

To lyse bacterial cells in each microtiter well and to expose the DNA, lysozyme and lysostaphin were added to the wells at final concentrations of 1 mg/ml and 100 µg/ml, respectively. The samples were incubated at 37° C. for 30 minutes prior to the addition of proteinase K and Tween 20 to final concentrations of 100 µg/ml and 1% (V/V), respectively. An additional 30 minutes of incubation at 55° C. was allowed to complete the lysis procedures before the enzymes were inactivated at 95° C. for 10 minutes.

Bacterial DNA molecules were amplified in 40 µl PCR mixture consisting of 4 µl of 10×buffer solution (100 mM Tris-HCl, pH 8.8, 1.5 mM $MgCl_2$, 50 mM KCl, and 0.1% Triton X-100), 0.125 µl each of 20 µM PCR primers with nucleotide sequences 5'-AGGAGGTGATCCAACCGCA and 5'-AACTGGACCAAGGTGGGGAG, 0.2 µl of 10 mM dNTP mixture, 12 µl of bacterial lysate, 0.5µ of 2U/µl polymerase (Dynazyme), and 23.1 μl of H$_2$O. Additional 15 μl of mineral oil was added to prevent evaporation. The microtiter plate containing the PCR mixtures was placed in a 96-well block thermal cycler (PTC-100, MJ Research, Inc.). The thermal cycler was set to 94° C. for 7 minutes followed by 25 cycles of the following temperature profiles, 95° C. for 45 seconds, 55° C. for 30 seconds, 72° C. for 40 seconds, and a final extension at 72° C. for 5 minutes.

After DNA amplification, the products were transferred to a flat bottom 96-well microtiter plate and YOYO-1 dye (Molecular Probes, Eugene, Oreg.) in 0.1×TAE buffer solution was added to the wells to make final dye concentration of 0.5 μM. The concentrations of amplified DNA were measured in less than one minute by an in-house constructed laser induced fluorescence microtiter plate reader which was consisted of an argon ion laser, photomultiplier tube, detection electronic circuits, and a computer controlled X-Y translation stage. The fluorescence image acquired by the scanning system was pseudo-color encoded for easy identification of differences in fluorescence intensity.

Figure 3:
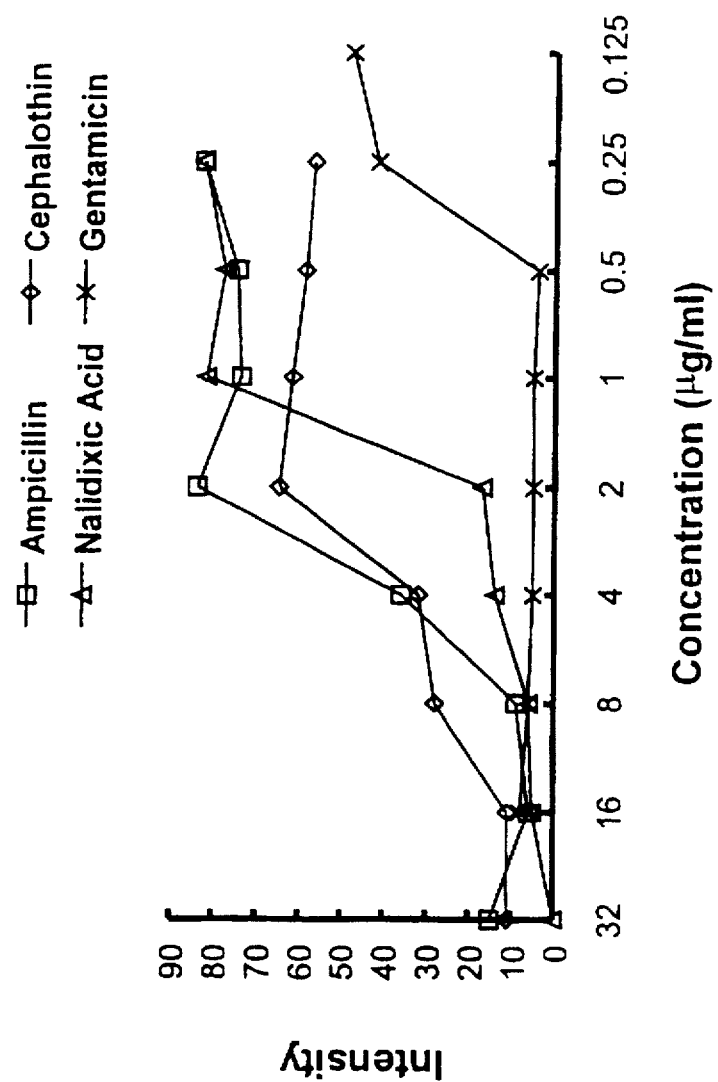
FIG. 3 shows the antimicrobial susceptibility testing results of four antibiotics to E. coli strain ATCC 25922: ampicillin (—▭—); cephalothin (—◆—); nalidixic acid (—▲—); and gentamicin (—✕—). The MIC values agree well with the values published by NCCLS.

The results are shown in FIG. 3. The MIC values reported by this invention agree well with the above tabulated MIC values published by NCCLS.

EXAMPLE 2

With a similar process, the MIC values for various antimicrobial agents to reference bacterial strains *Pseudomonas aerugenosa* ATCC 27853, *Staphylococcus aureus* ATCC 29213, *Escherichia coli* ATCC 25922 were determined. The MIC values for a panel of antibiotics were read under UV illumination in just a few seconds by observing the plates with or without the aid of a CCD camera and integrator. In such embodiment, the intercalating dye added to the wells has absorption within the UV region. For instance, ethidium bromide was added to the wells to final concentration of 3 μM and the microtiter plate was placed on top of a UV light box that output 313 nm wavelength UV light or be illuminated by UV light from above. The fluorescence emission of the ethidium bromide intercalated DNA can be viewed through a bandpass filter with center wavelength around 610 nm.

The susceptibility testing results of various antimicrobial agents to the three bacterial strains by this invention, the in vitro DNA amplification and fluorescence emission (DAFE) method, are summarized in the following table.

| Antimicrobial agent | Bacterial Strain | MIC range (μg/ml) NCCLS | DAFE |
|---|---|---|---|
| Ampicillin | E. coli | 2–8 | 4–16 |
| Carbenicillin | (ATCC 25922) | 4–16 | 16–32 |
| Cephalothin | | 4–16 | 4–32 |
| Cefuroxime | | 2–8 | 4 |
| Cefotaxime | | 0.06–0.25 | 1 |
| Ceftriaxone | | 0.03–0.12 | 0.06–0.12 |
| Gentamicin | | 0.25–1 | 0.5 |
| Norfloxacin | | 0.03–0.12 | 0.03–0.06 |
| Nalidixic Acid | | 1–4 | 2–8 |
| Cephalothin | S. aureus | 0.12–0.5 | 0.12–0.5 |
| Clindamicin | (ATCC 29213) | 0.06–0.25 | 0.06 |
| Erythromicin | | 0.12–0.5 | 0.06–0.12 |
| Gentamicin | | 0.12–1 | 0.12–0.25 |
| Norfloxacin | | 0.5–2 | 1–2 |
| Penicillin G | | 0.25–1 | 0.25–1 |
| Rifampin | | 0.008–0.06 | 0.004–0.015 |
| Trimethoprim | | 1–4 | 1–2 |
| Vancomycin | | 0.5–2 | 1 |
| Carbenicillin | P. aeruginosa | 16–64 | 16–64 |

-continued

| Antimicrobial agent | Bacterial Strain | MIC range (μg/ml) NCCLS | DAFE |
|---|---|---|---|
| Ceftriaxone | (ATCC 27853) | 8–32 | 8–32 |
| Gentamicin | | 1–4 | 0.25–1 |

We claim:

1. A method for antimicrobial susceptibility testing which comprises:
   incubating specimens of microbe(s) or microorganism(s) in media embedded with antimicrobial agents of serial dilution concentrations for a period of time sufficient to create differential microbial or microorganism counts in test samples; amplifying the differential microbial or microorganism counts by in vitro DNA replication of DNA from the samples; adding reporter molecules to said samples, wherein said reporter molecules are specific for double stranded DNA (dsDNA), allowing complexes to form between said reporter molecule and dsDNA in samples; and observing the presence or absence of signal from the reporter molecule added to the sample, wherein said method can be completed in 12 hours.

2. A method as in claim 1, wherein a rapid determination of MIC values for tested antimicrobial agents is determined by recording the lowest concentration of antimicrobial agent which results in no detectable signal from tested samples as the MIC values.

3. A method as in claim 1, wherein the period of time to create differential microbial counts is short.

4. A method as in claim 1, wherein the period of time to create differential microbial counts is at least one hour.

5. A method as in claim 1, wherein wherein no primary culture of specimen is involved.

6. A method as in claim 1, wherein no prior pathogen identification is involved.

7. A method as in claim 1, wherein the microbe or microorganism are lysed and its DNA exposed without removing media components by centrifugation or other separation process.

8. A method as in claim 7, wherein the microbial DNA are amplified without removing lytic reagents by centrifugation or other separation process.

9. A method as in claim 7, wherein the concentration of inhibiting components selected from the group consisting of lytic reagent, cell culture media component, and cellular debris is reduced.

10. A method as in claim 1, wherein the microbial concentration is less than 10$^5$ CFU/ml.

11. A method as in claim 1, wherein in vitro DNA replication is performed by a thermal cycling DNA polymerase chain reaction amplification method.

12. A method as in claim 11, wherein the thermal cycling DNA amplification method uses thermal stable enzyme.

13. A method as in claim 12, wherein the number of cycles of polymerase chain reaction amplification is less than 30 cycles.

14. A method as in claim 1, wherein in vitro DNA replication is performed by an isothermal amplification method.

15. A method as in claim 14, wherein the isothermal amplification method is strand displacement amplification.

16. A method as in claim 14, wherein the isothermal amplification method is self-sustained sequence replication method (3SR).

17. A method as in claim 1, wherein in vitro DNA replication amplifies a target DNA nucleotide sequence which encodes for the 16S rRNA gene.

18. A method as in claim 1, wherein the in vitro DNA replication target DNA specifically distinguishes as to which group of prokaryotic organisms the tested microbial belongs.

19. A method as in claim 1, wherein the in vitro DNA replication target DNA specifically identifies the group of fungi to which the tested microbial belongs.

20. A method as in claim 1, wherein the in vitro DNA replication target DNA specifically identifies the Mycobateriacea family.

21. A method as in claim 1, wherein the in vitro DNA replication is performed in a multi-well plate.

22. A method as in claim 1, wherein the reporter molecule contains a fluorescent intercalating dye.

23. A method as in claim 22, wherein a detected signal is from the flouresecnet dye molecule of the reporter molecule, intercalating with the dsDNA, said signal being greater than when the fluorescent dye is not intercalated with dsDNA.

24. A method as in claim 22, wherein the flourescent molecule is phenanthridinium monomer.

25. A method as in claim 22, wherein a flourescent signal is induced from the reporter molecule by UV excitation of the reporter molecule.

26. A method as in claim 25, wherein the UV excitation is at a wavelength of between 250 nm and 400 nm.

27. A method as in claim 22, wherein a fluorescent signal is induced from the reporter molecule by laser excitation.

28. A method as in claim 22, wherein the flourescent molecule is ethidium bromide.

29. A method as in claim 22, wherein the flourescent molecule is a multimer.

30. A method as in claim 22, wherein the flourescent molecule comprises a phenanthridine subunit.

31. A method as in claim 22, wherein the flourescent molecule is a dimer, and at least one of said molecules of the dimer is an acridine molecule.

32. A method as in claim 26, wherein MIC values of tested antimicrobial agents is determined by manual reading.

33. A method as in claim 26, wherein MIC values of tested antimicrobial agents is determined by an electronic device.

34. A method as in claim 33, wherein the electronic device comprises a photomultiplier tube, detector, and computer.

* * * * *